United States Patent [19]

Casey et al.

[11] Patent Number: 5,618,706
[45] Date of Patent: Apr. 8, 1997

[54] PREPARATION OF PHYTOSPHINGOSINE DERIVATIVE

[75] Inventors: John Casey, Wellingborough; Katherine A. Maume, Camberly, both of Great Britain; Alfons L. J. Peters, Bussum; Rudolf M. Veloo, Naarden, both of Netherlands

[73] Assignee: Quest International B.V., Naarden, Netherlands

[21] Appl. No.: 494,850

[22] Filed: Jun. 26, 1995

[30] Foreign Application Priority Data

Jun. 24, 1994 [EP] European Pat. Off. .............. 94201825

[51] Int. Cl.$^6$ .................. C12P 13/00; C12N 1/16
[52] U.S. Cl. ............. 435/128; 435/101; 435/255.5; 435/938
[58] Field of Search ................. 435/128, 101, 435/938, 255.5

[56] References Cited

U.S. PATENT DOCUMENTS

| | | | |
|---|---|---|---|
| H001,168 | 4/1993 | McKeena et al. | 514/28 |
| 5,262,312 | 11/1993 | Holla et al. | 435/101 |
| 5,368,857 | 11/1994 | Corcoran | 424/401 |

*Primary Examiner*—Herbert J. Lilling
*Attorney, Agent, or Firm*—Cushman Darby & Cushman IP Group Pillsbury Madison & Sutro LLP

[57] ABSTRACT

The invention concerns a process for preparing tetraacetylphytospingosine (TAPS) using F-60-10 mating type strain of *Pichia ciferrii*. Such strain is subjected to mutagenesis and the high TAPS producing strains are selected by a special procedure. These strains are grown in a fed batch mode on a non-fermentative carbon source at a temperature above 26° C and the TAPS collected from the fermentation medium. Glycerol is a preferred carbon source and preferably L-serine is added to the culture medium.

12 Claims, No Drawings

PREPARATION OF PHYTOSPHINGOSINE DERIVATIVE

The invention concerns a process for the microbiological preparation of certain phytosphingosine derivatives. More particularly the invention concerns a process for the preparation of tetraacetyl-phytosphingosine.

It is generally understood that ceramides and related lipid compounds, often generally referred to as sphingolipids, are present in the stratum corneum of the skin and play an important role in preventing excessive water-loss and dry out of the skin. In EP-B-0 097 059 their role in the water barrier function of the skin is outlined. Also in this patent and in GB 2 178 312 and 2 213 723 the use of ceramides and like lipids in compositions for topical application is described to aid in restoring the water barrier function of aging and dry skin.

Ceramides are N-acylated sphingosine bases in which the acyl group is derived from various long chain fatty acids. Such ceramides have been obtained primarily from various animal and to a lesser extent vegetable sources, but the products thus obtained are not always acceptable for cosmetic purposes or need extensive purification.

A wealth of literature on the structure of ceramides exists. Recently synthetic ceramides and ceramide analogues have been described in EP-B-0 097 059, EP-A-0 420 722 and EP-A-0 500 437. These ceramides and analogues have been synthesized from various sphingosine bases. Various routes for obtaining sphingosines are also described by D. Shapiro in "Chemistry of Sphingolipids", Hermann, Paris (1969). One type of sphingosine bases is phytosphingosine having the structure:

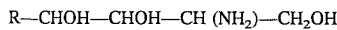

wherein R is a long straight chain alkyl group, particularly $C_{14}H_{29}$. This is the base component in ceramides 3 and 6b identified in the lipids of the human skin. Thus, there is a need for an efficient synthesis of phytosphingosine, which should moreover preferably provide the right stereoisomer, i.e. the one that is present in the lipids of the skin.

In various publications it is described that the non-pathogenic yeast *Hansenula ciferrii*, also named *Pichia ciferrii* (hereinafter referred to as *P ciferrii*) is able to produce tetraacetylphytospingosine, hereinafter referred to as TAPS, in small quantities, see:

L. J. Wickerham & F. H. Stodola, J. Bacteriol. 80 (1960), 484–491

H. G. Maister et al, Appl. Microbiol. 10 (1962), 401–406,

M. L. Greene et al, Biochim. Biochem. Biophys. 143 (1965), 553–565,

R. Kulmacs & G. Schroepfer, Biochem. & Biophys Res. Comm. 82:1 (1978), 371–377,

Y. Barenholtz et al, Biochim & Biophys Acta, 248 (1971), 458–465,

Y. Barenholtz et al, Biochim & Biophys Acta, 306 (1973), 341–345.

Maister, using the F-60-10 mating type strain, was able to produce up to 300 mg/l in a pilot scale batch mode fermentation using glucose as a carbon source at 25° C. The TAPS produced is the D-D-erythro isomer, which has the same stereochemistry as the phytosphingosine occurring in the human skin. TAPS may be easily deacetylated to phytosphingosine. However, the yields of TAPS are too low to be of any practical value for commercial production.

A process has now been found for producing commercial quantities of TAPS by growing F-60-10 mating type strain of *Pichia ciferrii* which comprises the steps of:

I subjecting a F-60-10 mating type strain of *Pichia ciferrii* to mutagenesis;

II selecting the high TAPS producing mutant strains of *Pichia ciferrii*;

III growing the selected strains in a fed-batch mode on a non-fermentative carbon source at a temperature above 26° C.;

IV collecting the TAPS produced or the hydrolysis product thereof from the culture medium.

For step I classical mutagenesis techniques can be used e.g. treatment of the cells with ultraviolet radiation or with mutagenetic chemicals such as ethylmethanesulphonate (EMS), dimethylsulphate, diethylsulphate, N-methyl-N'-nitro-N-nitrosoguanidine, bromouracil and other nucleotide base analogues, and acridines. Such techniques are discussed in Shermal et al, Methods in Yeast Genetics, Cold Spring Harbor Laboratory, 1979 and other texts known to those skilled in the art.

The cells so treated are plated out in a conventional way, preferably on a non-fermentative medium and the surviving colonies are tested for their ability to produce TAPS. It has been found that relatively small colonies having a rough convex surface appearance, in comparison with the smooth surface appearance of other colonies, have the highest chance of being high producers of TAPS. Under a microscope thin needle-like crystals of TAPS are often visibl in the colonies which is another indication of a high TAPS producing strain.

The promising strains are further tested on their TAPS producing ability in shake flask cultures using a medium with a non-fermentative carbon source. Only strains producing at least 0.5 g/l TAPS, preferably at least 0.8 g/l, more preferably at least 1.0 g/l in the Selection Procedure described below were selected for further use.

Thus, the invention also provides strains of F-60-10 mating type *P ciferrii* which area able to produce at least 0.8 g/l, more preferably at least 1.0 g/l of TAPS in the culture broth when grown under batch culture conditions, more specifically under the batch culture conditions used in the Selection Procedure. Such strains may be obtained according to the invention by mutation of the known F-60-10 mating type *P ciferrii* strain.

The selected strains can be used to produce TAPS on a commercial scale by growing in in a fed-batch mode on a nonfermentative carbon source. Suitable carbon sources are e.g. glycerol, gluconate, citrate, lactate, xylitol and ethanol. Glycerol is a particularly suitable and economical carbon source. The carbon source is already present in the culture broth at the beginning of the fermentation, preferably in a concentration of at least 10 g/l and further added during the fermentation, either at intervals or continuously so as to maintain growth. Preferably the carbon source is added at such a rate that not the carbon source concentration but rather the availability of oxygen in the culture broth is limiting for the speed of biomass formation.

In the literature *P ciferrii* is consistently cultured at temperatures around 25° C. However, in the process of the invention culturing is done above 26° C., preferably between 28° and 33° C., more preferably around 30° C.

Greene (vide supra) has shown that serine and palmitate are both involved in the synthesis of TAPS by *P ciferrii* on a 1:1 molar basis. In the process of the present invention the addition of serine has a positive influence on the production of TAPS and thus serine may be advantageously added to the culture broth in a concentration of up to 20 g/l, preferably up to 10 g/l, more preferably up to 6 g/l.

However, it has been found that the addition of palmitate does not appreciably increase TAPS production and that at any rate the palmitate concentration is preferably kept below 10 g/l of the culture broth and also be less than equimolar to the serine concentration. Serine, and possibly palmitate, are preferably also added in a fed-batch mode.

The process yields a mixture of phytosphingosines of varying degrees of acetylation and various chain lengths i.e. R is between C12 and C16. However, tetraacetylphytosphingosine with R is C14 is the predominant product.

The TAPS (which for the purpose of this invention is meant to comprise the total phytosphingosine mixture) may be isolated from the culture broth in ways known in the art, particularly by extraction with an organic solvent. This may be done before separation of the biomass from the broth, however, in a preferred procedure the biomass is first separated from the broth in a conventional way such as by centrifugation or filtration. The TAPS may then be extracted from the biomass with a suitable organic solvent, such as methanol, ethanol, isopropanol, ethyl acetate, hexane or the like. In a preferred procedure a small amount of acetic acid e.g. 1% w/w is added to the solvent before it is used for extraction. The biomass may be extracted in a wet state, or it may first be dried, e.g. by freeze drying. An additional quantity of TAPS may be obtained by extraction of the supernatant obtained after separation of the biomass from the broth.

Alternatively, the TAPS may first be subjected to alkaline hydrolysis in the broth to yield phytosphingosine, which may thereafter be extracted, and reconverted to TAPS if desired.

The TAPS (or phytosphingosine) may be further purified by recrystallization (e.g. from methanol or isopropanol) or column chromatography on silica gel.

The TAPS may be hydrolysed to phytosphingosine having the desired D-D-erythro configuration. The phytosphingosine (or phytosphingosine mixture) thus obtained may be converted to ceramides in ways known in the art.

Selection Procedure for mutant strains.

A loop of a promising colony is placed in a 50 ml baffled shake flask containing 25 ml of culture medium of the following composition (conc. in g/l):

2.0 $KH_2PO_4$ 1.5 $MgSO_4 \cdot 7H_2O$ 5.0 $(NH_4)_2PO_4$ 0.5 KCl 5.0 Yeast extract (Difco)

30.0 Glycerol 5.0 L-serine

The flask is placed in a Gallenkamp shake incubator and incubated at 150–200 rpm and 30° C. for 7 days. Thereafter the contents are analysed for dry matter and TAPS concentration.

Dry matter is determined by spinning down a sample of 3 ml broth in a weighed tube. After decanting the supernatant the remaining biomass is dried overnight at 110° C. After cooling the closed tube the biomass is determined by weighing the tube.

TAPS concentration is determined by GLC. A known amount of broth to which a known amount of methyl stearate is added as an internal standard, is extracted with a 4:1 mixture of ethyl acetate and methanol.

EXAMPLE 1

*P ciferrii* mating type F-60-10 (NRRL Y1031) strain was mutant using ethylmethanesulphonate (EMS) according to the following procedure:

The strain was cultured in microphil broth (10 g/l soymeal peptone, 10 g/l glucose, 1 litre distilled water, pH 5.0). Following 2–3 days incubation at 30° C. in an orbital shaker, when the cells were in late log phase of growth, 10 ml of broth was collected and aseptically centrifuged. The cell mass obtained following removal of the supernatant, was aseptically mixed with a 10 ml sterile solution of phosphate buffer, 0.1M. pH 7.0. The resulting mixture was shaken, spun down and the pellet containing the biomass was collected. To the pellet 1 ml phosphate buffer (as above) was added together with 5, 40 or 100 ul of the mutagen EMS.

The solutions were thoroughly mixed, and incubated for one further hour at 30° C. After this time, 9 ml of a 5% w/v solution $Na_2S_2O_3$ was added in order to inactivate the mutagen. After 10 min. the samples were again spun down and redissolved in 9 ml of a 5% w/v $Na_2S_2O_3$ solution. Again the cells were separated by spinning and redissolved/washed twice in the phosphate buffer, dilutions made, and plated out onto the following glycerol medium (conc. in g/l):

1.0 $KH_2PO_4$ 0.7 $MgSO_4 \cdot 7H_2O$ 2.5 $(NH_4)_2HPO_4$ 0.2 KCl 0.5 Yeast extract (Difco)

20.0 Glycerol 5.0 Serine 15.0 Agar

Following 3 days incubation at 30° C., the surviving colonies were counted and the % kill calculated. Dilutions were prepared to give a colony count of 50 colonies per plate.

EXAMPLE 2

TAPS was produced by growing the selected strains according to the following procedure:

A seed culture for the fed-batch culture was grown by adding 1% of a selected strain to a 250 ml baffled shake flask containing 100 ml of the culture medium also used for the selection procedure. The flasks were incubated using the conditions described there.

For the actual TAPS production a 71 MBR Labfermenter with a working volume of 2.0–2.6l was used, stirred by two magnetically driven 6-blade Rushton-type impellers. pH and dissolved oxygen were measured by Ingold electrodes. Airflow was regulated at a set flow rate. The vessel with electrodes was in situ sterilised at 120° C. for 20 min. prior to inoculation with the seed culture. pH was controlled by addition of 10% NaOH solution. $DO_2$ and exhaust gas $CO_2$ and $O_2$ levels were measured and from this carbon production rate (CPR) and oxygen uptake rate (OUR) were calculated.

The culture medium had the following composition (conc. in g/l):

4.0 $KH_2PO_4$ 2.5 $MgSO_4 \cdot 7H_2O$ 10.0 $(NH_4)_2PO_4$ 1.0 KCl 10.0 Yeast autolysate 40.0 Glycerol 5.0 L-serine The culture conditions were as set out below:

| | |
|---|---|
| $DO_2$ | min 10% |
| Temperature | 30° C. |
| pH | 6.4 |
| Stirring rate | 800–1300 rpm |
| OUR | 100–170 mmol/l.min |
| Air flow | 0.5–1.0 vvm |
| Antifoam | 0.3 ml/l batch volume silicone oil |

10% v/v of the seed culture was added to the culture medium in the fermentor. When glycerol in the batch was depleted as indicated by analysis of the exhaust gas showing a drop in OUR (typically after a period of 20–25 hours), a feed solution of 50% w/w of glycerol and 4% w/w of L-serine in water was gradually fed into the fermentor in a quantity of 300 g/l working volume over a period of 15 hours. Total biomass and TAPS concentration were regularly monitored in samples taken from the fermentor which were analysed as described under the Selection Procedure above.

Typically maximum biomass levels of 60 g/l were reached for a total feed of 180–190 g/l of glycerol, yielding a TAPS concentration of at least 2.0 g/l Two mutant strains were identified which produced 3.8 g/l and 5.0 g/l of TAPS respectively and which are deposited with the Deutsche Sammlung von Mikroorganismen und Zellkulturen GmbH as DSM 9227 and DSM 9228.

The TAPS was isolated by separating the biomass from the culture broth by centrifugation. The wet cell mass was extracted with an equal weight quantity of isopropanol to which 1% w/w of acetic acid was added. The mixture was stirred for 15 minutes. Thereafter sodium chloride was added and mixed in an amount of ¼ of the amount of isopropanol, the mixture was allowed to stand and the isopropanol layer removed. Thereafter the wet cell mass was again extracted by stirring for 1 hour with the same amount of ethyl acetate (to which 1% w/w of acetic acid was added) and the organic layer removed. The combined organic layers were evaporated at 40° C. under reduced pressure and the oily residue further purified by column chromatography over silica gel. For each 1 g of oily residue 5 g of silica gel was used. The column is eluted with:

i. 1 column volume of hexane ii. 1 column volume of hexane/ethyl acetate 9:1 iii. 1 column volume of hexane/ethyl acetate 5:1 iv. 1 column volume of hexane/ethyl acetate 3:2 v. 1 column volume of ethyl acetate vi. 1 column volume of isopropanol vii. 1 column volume of isopropanol Fractions v. and vi. yielded 95% pure TAPS on concentration under reduced pressure. This could be further purified by recrystalization from isopropanol or butanol to which 1% w/w of acetic acid had been added.

We claim:

1. A process for producing Tetraacetyl-phytospingosine (TAPS) by growing a F-60-10 mating type strain of *Pichia ciferrii* which comprises the steps of:

I subjecting a F-60-10 mating type strain of *Pichia ciferrii* to mutagenesis;

II selecting the TAPS producing mutant strains of *Pichia ciferrii*;

III growing the selected strains in a fed-batch mode on a non-fermentative carbon source at a temperature above 26° C.;

IV collecting the TAPS produced or the hydrolysis product thereof from the culture medium.

2. A process according to claim 1 wherein the mutation is carried out by subjecting the strain to ethylmethanesulphonate.

3. A process according to claims 1 or 2 wherein a mutant strain is selected which produces at least 0.5 g/l TAPS in the selection procedure.

4. A process according to claim 3 wherein the mutant strain produces at least 0.8 g/l TAPS in the selection procedure.

5. A process according to claim 4 wherein the mutant strain produces at least 1.0 g/l TAPS in the selection procedure.

6. A process according to claim 1 wherein a selected strain is is grown on glycerol as the non-fermentative carbon source.

7. A process according to claim 1 wherein a selected strain is grown at a temperature between 28° and 33° C.

8. A process according to of claim 1 wherein L-serine is added to the culture medium.

9. A process according to claim 1 wherein the glycerol is fed to the culture medium at such a rate that the availability of oxygen is determining for the speed of biomass formation.

10. A process for producing phytosphingosines wherein TAPS produced according to claim 1 is hydrolysed.

11. A process according to claim 10 wherein the hydrolysis is done with alkali.

12. A process according to claim 11 wherein the hydrolysis is carried out in the culture broth before separation of the TAPS from the culture broth.

* * * * *